United States Patent [19]

VandenBerg

[11] Patent Number: Plant 7,434

[45] Date of Patent: Jan. 29, 1991

[54] CHRYSANTHEMUM PLANT NAMED SONRISA

[75] Inventor: Cornelis P. VandenBerg, Salinas, Calif.

[73] Assignee: Yoder Brothers, Inc., Barberton, Ohio

[21] Appl. No.: 435,824

[22] Filed: Nov. 14, 1989

[51] Int. Cl.[5] ..... A01H 5/00

[52] U.S. Cl. ..... Plt./74

[58] Field of Search ..... Plt./74

*Primary Examiner*—James R. Feyrer

*Attorney, Agent, or Firm*—Foley & Lardner, Schwartz, Jeffery, Schwaab, Mack, Blumenthal & Evans

[57] ABSTRACT

A Chrysanthemum plant named Sonrisa particularly characterized by its flat capitulum form, daisy capitulum type; white ray floret color with a distinct red-brown dot in the center of the disc; diameter across face of capitulum of up to 7 cm at maturity; uniform eight week photoperiodic flowering response to short days; peduncle length ranging from 10 to 20 cm on open, terminal sprays; short plant height when grown as a single stem spray cut mum; and excellent tolerance to low temperatures for bud initiation and flower development.

3 Drawing Sheets

The present invention comprises a new and distinct cultivar of Chrysanthemum, botanically known as *Dendranthema grandiflora*, and referred to by the cultivar name Sonrisa.

Sonrisa, identified as 84-539005, was originated from a cross made by Cornelis P. VandenBerg in a controlled breeding program in Salinas, Calif., in 1984.

The female parent of Sonrisa was the cultivar identified as Frost, disclosed in U.S. Plant Pat. No. 4,129. The male parent of Sonrisa was an unnamed seedling identified as 79-R99007, and described as a white daisy cut spray mum, with medium plant height and nine week photoperiodic flowering response.

Sonrisa was discovered and selected as one flowering plant within the progeny of the stated cross by Cornelis P. VandenBerg in May of 1985, in a controlled environment in Salinas, Calif.

The first act of asexual reproduction of Sonrisa was accomplished when vegetative cuttings were taken from the initial selection in July 1985 in a controlled environment in Salinas, Calif., by technicians working under formulations established and supervised by Cornelis P. VandenBerg.

Horticultural examination of controlled flowerings of successive plantings has shown that the unique combination of characteristics as herein disclosed for Sonrisa are firmly fixed and are retained through successive generations of asexual reproduction.

Sonrisa has not been observed under all possible environmental conditions. The phenotype may vary significantly with variations in environment such as temperature, light intensity and daylength.

The following observations, measurements and comparisons describe plants grown in Salinas, Calif. under greenhouse conditions which approximate those generally used in commercial greenhouse practice. The low temperature tolerance of the new variety as noted below was determined in repeated flowerings in Bogota, Colombia.

The following traits have been repeatedly observed and are determined to be basic characteristics of Sonrisa, which, in combination, distinguish this Chrysanthemum as a new and distinct cultivar:

1. Flat capitulum form.
2. Daisy capitulum type.
3. White ray floret color, with a distinct red-brown dot in the center of the disc.
4. Diameter across face of capitulum up to 7 cm at maturity.
5. Uniform eight week photoperiodic flowering response to short days.
6. Peduncle length ranging from 10 to 20 cm on open, terminal sprays.
7. Short plant height, requiring two to three long day weeks prior to short days to attain a flowered plant height of 90 to 100 cm for year-round flowerings.
8. Excellent tolerance to low temperatures for bud initiation and flower development.

The accompanying photographic drawings show typical inflorescence and leaf characteristics of Sonrisa, with the colors being as nearly true as possible with illustrations of this type. Sheet 1 is a color photograph of Sonrisa grown as a single stem cut spray mum. Sheet 2 is a black and white photograph of three views of the inflorescence of Sonrisa. Sheet 3 is a black and white photograph showing the upper and under sides of the leaves of Sonrisa at three stages of development (mature, intermediate and immature).

Of the commercial cultivars known to the inventor, the most similar in comparison to Sonrisa is the cultivar identified as Nevado, disclosed in U.S. Plant patent application Ser. No. 210,004, now U.S. Plant Pat. No. 7,019. Reference is made to attached Chart A, which compares certain characteristics of Sonrisa to the same characteristics of Nevado.

Similar traits are ray floret color, capitulum form and type, spray formation, peduncle length, diameter of capitulum and low temperature tolerance. Sonrisa has a shorter plant height and a faster flowering response than Nevado. In addition, Sonrisa has a very distinct red-brown dot in the center of the disc and shows a very slight pinking of buds under low temperatures. Nevado has an immature green disc which matures to yellow and never shows pinking of buds on flower.

In the following description color references are made to The Royal Horticultural Society Colour Chart.

The clear white ray floret color of Sonrisa is not represented in the R.H.S. Colour Chart. The color values were determined on plant material grown in Salinas, Calif. on July 18, 1989.

Classification:

*Botanical.*—*Dendranthema grandiflora* cv Sonrisa.

*Commercial.*—Daisy cut spray mum.

INFLORESCENCE

A. Capitulum:

*Form.*—Flat.

*Type.*—Daisy.

*Diameter across face.*—Up to 7 cm at maturity.

B. Corolla of ray florets:

*Color (general tonality from a distance of three meters).*—White.

*Color (upper surface).*—Clear white.

*Color (under surface).*—Clear white. When grown under low temperatures, the buds show a very slight overcast of 49D.

*Shape.*—Straight, cross-section slightly ribbed, apex convex, base concave.

C. Corolla of disc florets:

*Color (mature).*—Closest to 17A.

*Color (immature).*—Closest to 144B. The disc shows a very distinct red-brown center, closest to 183A to 183B.

D. Reproductive organs:

*Androecium.*—Present on disc florets only; scant to moderate pollen.

*Gynoecium.*—Present on both ray and disc florets.

PLANT

A. General appearance:

*Height.*—Short; 90 to 100 cm as a single stem cut mum with two to three long day weeks prior to short days.

B. Foliage:

*Color (upper surface).*—147A.

*Color (under surface).*—147B.

*Shape.*—Lobed, slightly serrated.

I claim:

1. A new and distinct Chrysanthemum plant named Sonrisa, as described and illustrated.

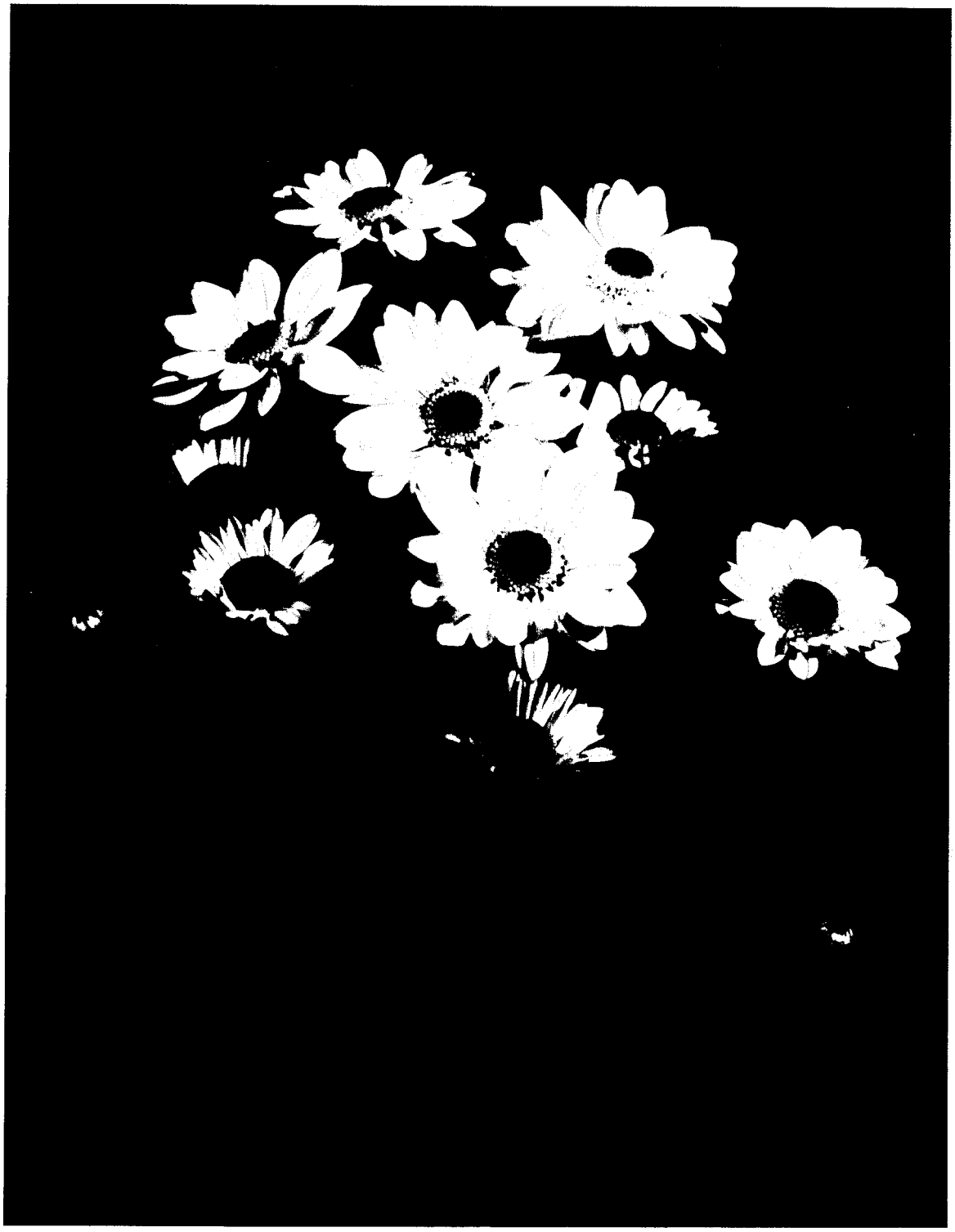

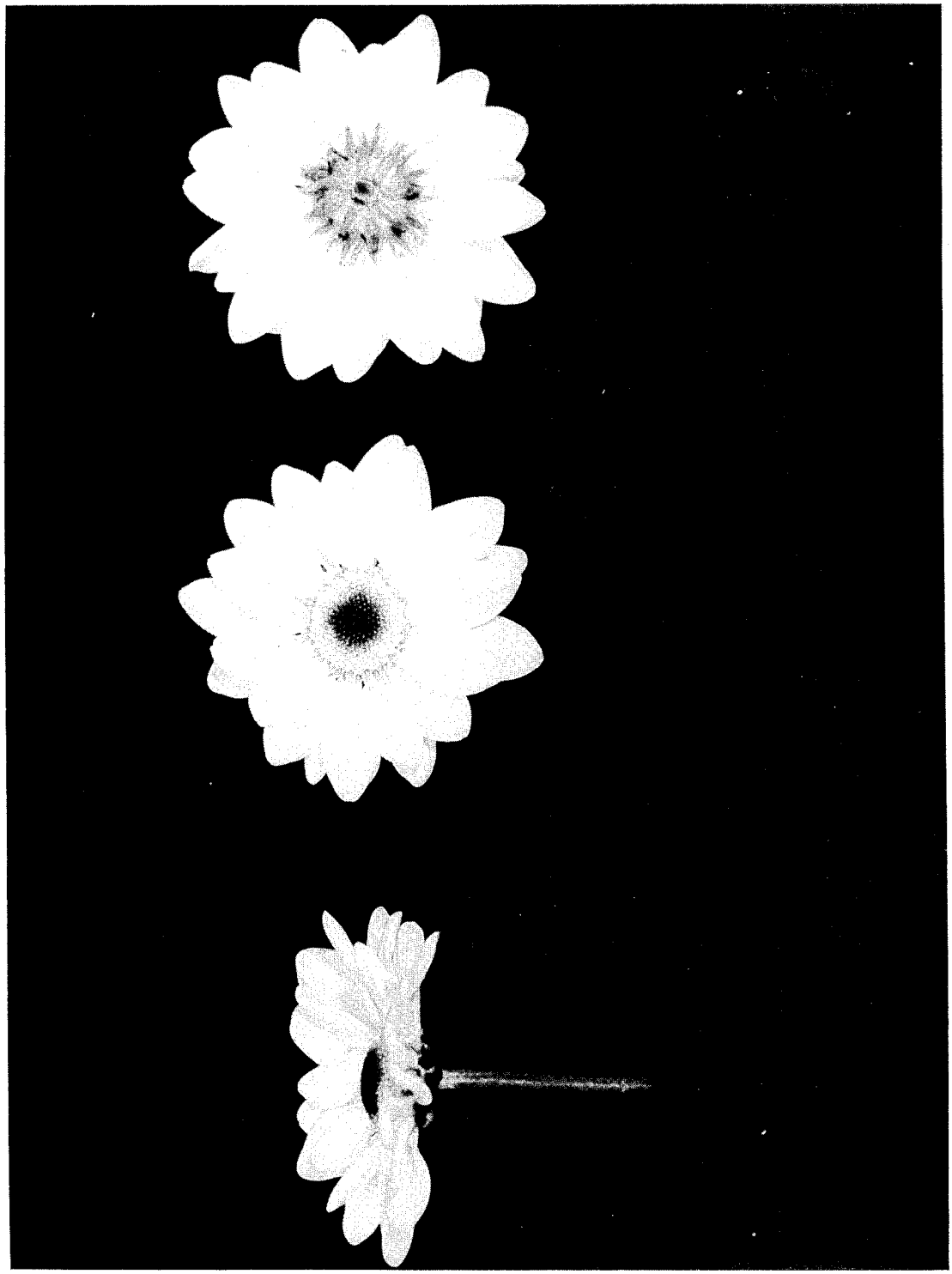

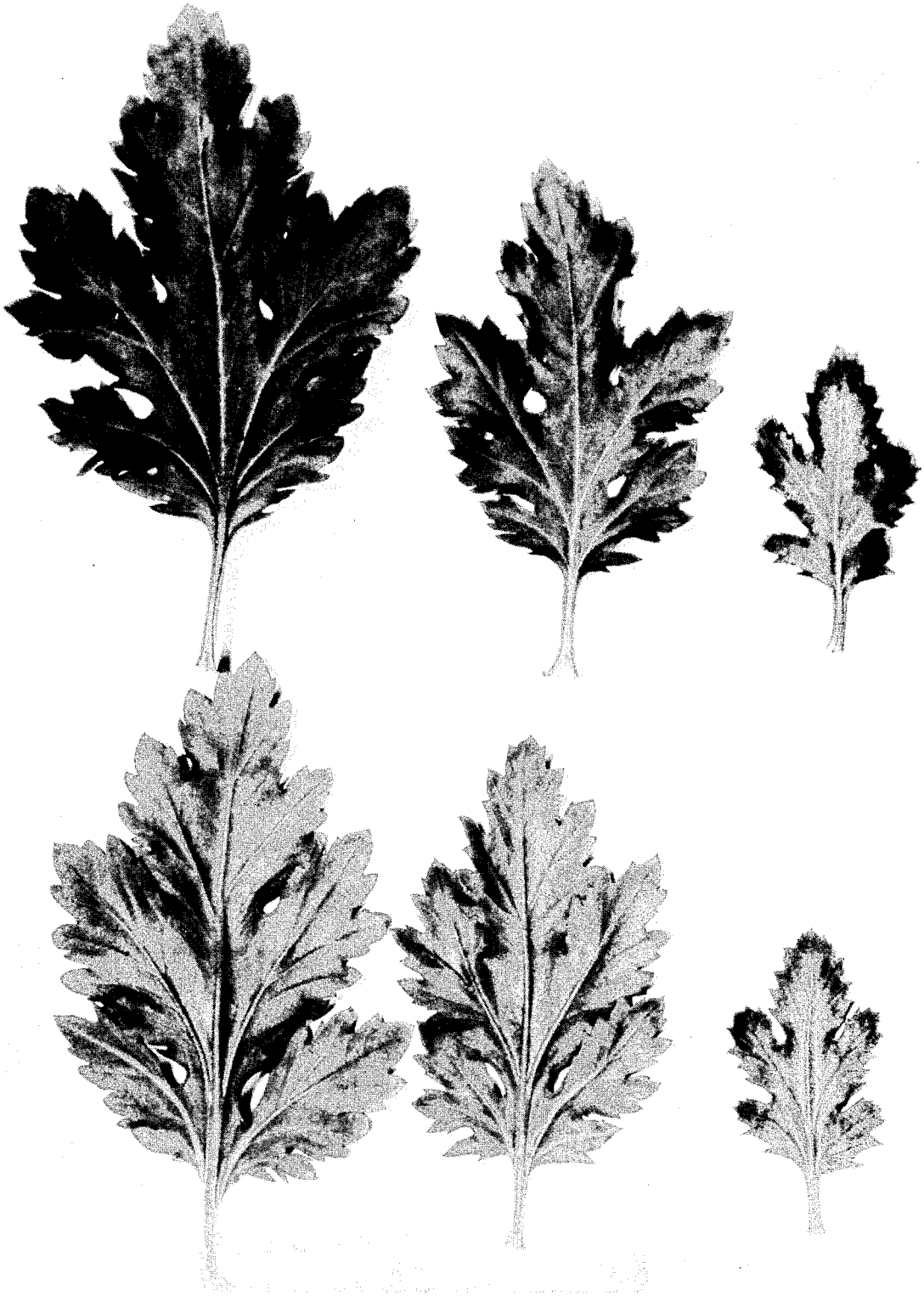

* * * * *